US012644021B2

(12) United States Patent
Daily

(10) Patent No.: US 12,644,021 B2
(45) Date of Patent: Jun. 2, 2026

(54) ORTHOPEDIC THERAPY APPARATUS

(71) Applicant: Daily Products Inc, Sheridan, WY (US)

(72) Inventor: David Daily, Los Angeles, CA (US)

(73) Assignee: Daily Products Inc, Los Angeles, CA (US)

( * ) Notice: Subject to any disclaimer, the term of this patent is extended or adjusted under 35 U.S.C. 154(b) by 0 days.

(21) Appl. No.: 19/071,900

(22) Filed: Mar. 6, 2025

(65) Prior Publication Data

US 2025/0197679 A1 Jun. 19, 2025

Related U.S. Application Data

(62) Division of application No. 18/046,412, filed on Oct. 13, 2022, now Pat. No. 12,275,871.

(51) Int. Cl.
| | |
|---|---|
| *A61F 13/00* | (2024.01) |
| *A61F 5/01* | (2006.01) |
| *A61F 13/02* | (2006.01) |
| *C09J 7/00* | (2018.01) |
| *C09J 7/20* | (2018.01) |
| *C09J 7/40* | (2018.01) |

(52) U.S. Cl.
CPC ..................................... *C09J 7/00* (2013.01); *A61F 5/01* (2013.01); *A61F 13/0273* (2013.01); *C09J 7/20* (2018.01); *A61F 13/023* (2013.01); *C09J 7/40* (2018.01); *Y10T 156/1051* (2015.01)

(58) Field of Classification Search
None
See application file for complete search history.

(56) References Cited

U.S. PATENT DOCUMENTS

| | | | | |
|---|---|---|---|---|
| 2,852,026 A | * | 9/1958 | Karr | .................. A61F 13/47236 604/377 |
| 3,920,017 A | * | 11/1975 | Karami | ............. A61F 13/53418 604/389 |
| 4,519,800 A | * | 5/1985 | Merry | ............... A61F 13/49003 604/385.25 |

(Continued)

FOREIGN PATENT DOCUMENTS

GB 816508 A * 7/1959

*Primary Examiner* — Kim M Lewis
(74) *Attorney, Agent, or Firm* — Briggs IP; Jeremy A. Briggs

(57) ABSTRACT

An orthopedic therapy apparatus having a plurality of elongated therapy tapes is disclosed. Each elongated therapy tape includes a deformable textile body having an adhesion surface and a non-adhesion surface. Each elongated therapy tape may include a first adhesion pad surface disposed on the adhesion surface at a deformable textile body proximal end, and a second adhesion pad surface disposed on the adhesion surface at a deformable textile body distal end. Each elongated therapy tape may include a first adhesion surface side portion disposed proximate to an orthopedic therapy apparatus edge along a deformable textile body longitudinal axis, and a second adhesion surface side portion disposed proximate to an orthopedic therapy apparatus opposite edge. Each elongated therapy tape may include a first pair of separating cuts proximate to the deformable textile body proximal end, and a second pair of separating cuts proximate to the deformable textile body distal end.

20 Claims, 6 Drawing Sheets

(56)                    References Cited

U.S. PATENT DOCUMENTS

| | | | | |
|---|---|---|---|---|
| 8,147,472 B2 * | 4/2012 | Venturino | ......... | A61F 13/15699 |
| | | | | 604/385.201 |
| 2016/0174643 A1 * | 6/2016 | Miller | ........................ | C09J 7/20 |
| | | | | 156/249 |

* cited by examiner

300

306

304b

302b

304a

302a

300

302b

302a

306

308b

308a

ORTHOPEDIC THERAPY APPARATUS

CROSS-REFERENCE TO RELATED APPLICATIONS

This application is a divisional application of co-pending prior U.S. patent application Ser. No. 18/046,412, filed Oct. 13, 2022, the entire contents of which are incorporated herein by reference thereto.

TECHNICAL FIELD

The present disclosure relates to an orthopedic therapy apparatus, and more specifically to an orthopedic therapy tape having a deformable textile body that may be configurable to various shapes for convenient use to limit body motion.

BACKGROUND

Therapists recommend patients recovering from therapeutic treatments to limit physical movement of affected limbs. Limiting limb movement may help in faster patient recovery, for example, after an injury or during recovery from an operative procedure. In addition, the patient may experience less pain and discomfort during post injury recovery phase, when the patient restricts the limb movement.

Therapists typically restrict the patient limb movement by applying stretchable or semi-stretchable adhesive tapes over the affected limbs. Along with limiting limb movement, the adhesives tapes act as a physical reminder to the patients that certain movements may be undesirable.

Some conventional adhesive tapes use adhesive-backed cloth tape materials having deformable characteristics. The cloth tape materials may include an adhesive surface on a backside and a cloth-like feel on a front side. The cloth tape materials provide various advantages over other tapes (such as sports tape), for example, the cloth tape materials are easily removable. However, the cloth tape materials are typically highly adhesive, and may cause discomfort to the patient, for example, when the tape is removed.

Further, conventional adhesive tapes have standard dimensions. For example, customizing length and/or width of a conventional tape may not be possible. Since limbs have different curvatures and sizes, using standard-sized adhesive tapes may cause inconvenience to patients.

Thus, there is a need for an orthopedic therapy tape that is convenient to use, and provides flexibility to the patients to customize the tape dimensions.

It is with respect to these and other considerations that the disclosure made herein is presented.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

Figure 1:
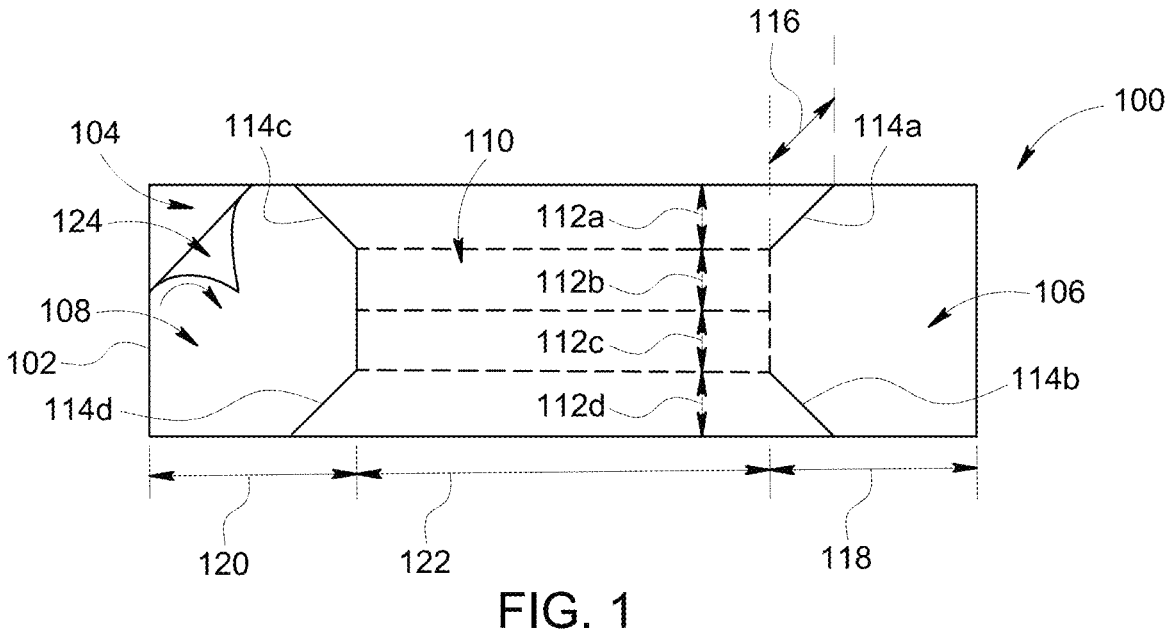
FIG. 1 depicts an orthopedic therapy apparatus in accordance with the present disclosure.

The present disclosure is directed towards an orthopedic therapy apparatus, such as an orthopedic therapy tape that a therapist may apply to a patient limb. The apparatus may be stretchable or semi-stretchable and may assist in limiting the patient limb movement, for example, when the patient undergoes an operative procedure on the limb. The apparatus may include a deformable textile body including an adhesion surface and a non-adhesion surface opposite to the adhesion surface. The deformable textile body may be made of, for example, cloth. The apparatus may further include a pair of adhesion pad surfaces disposed on the adhesion surface, and formed at deformable textile body proximal and distal ends. In addition, the apparatus may include a tension member disposed between the pair of adhesion pad surfaces. The tension member may be made of same material as the deformable textile body, for example, cloth. During application, the therapist may apply the apparatus to the patient limb by using the pair of adhesion pad surfaces. When applied, the tension member, which may be disposed over a substantial orthopedic therapy apparatus length, touches the patient limb along with the pair of adhesion pad surfaces.

In some aspects, the tension member may include a first folded side portion and a second folded side portion of the deformable textile body. The first folded side portion and the second folded side portion may fold around a deformable textile body longitudinal axis to contact and adhere to a deformable textile body middle portion. The first folded side portion and the second folded side portion may fold by using a plurality of separating cuts that may be disposed on the deformable textile body. In some aspects, the plurality of separating cuts may be at a predetermined angle from the deformable textile body longitudinal axis.

In one or more aspects, the orthopedic therapy apparatus may include a plurality of elongated therapy tapes that may be packaged as a strip, stack or roll of therapy tapes. A strip or roll of elongated therapy tapes may include a plurality of cut guides disposed on the strip/roll, to assist the therapist in customizing an orthopedic therapy apparatus length based on patient limb curvature and size.

The present disclosure discloses an orthopedic therapy apparatus that is convenient for a patient to wear. Specifically, of the three orthopedic therapy apparatus surfaces that touch the patient skin (e.g., the pair of adhesion pad surfaces and the tension member), only the pair of adhesion pad surfaces include adhesive. The tension member is made of textile material, for example, cloth, and is thus more comfortable for the patient to wear. In some aspects, a substantial portion of an orthopedic therapy apparatus length may include the tension member, and hence a substantial portion of orthopedic therapy tape length that touches the patient skin is non-adhesive (e.g., cloth). Thus, the orthopedic therapy apparatus is more comfortable for the patient to wear as compared to convention adhesive tapes, which include adhesives along a substantial tape area. Further, the therapist may customize the orthopedic therapy apparatus length for patients with different limb curvatures and sizes, which may result in greater patient comfort.

These and other advantages of the present disclosure are provided in detail herein.

Illustrative Embodiments

The disclosure will be described more fully hereinafter with reference to the accompanying drawings, in which example embodiments of the disclosure are shown, and not intended to be limiting.

FIG. 1 depicts an orthopedic therapy apparatus 100 in accordance with the present disclosure. The orthopedic therapy apparatus 100 may be, for example, an orthopedic therapy tape that may be applied to a patient limb, which may limit the limb movement. For example, a therapist or a doctor may apply the orthopedic therapy apparatus 100 to an affected patient limb, when the patient undergoes an operative procedure on the limb. In some aspects, the orthopedic therapy apparatus 100 may be stretchable or semi-stretchable, which may enable the therapist to apply the orthopedic therapy apparatus 100 on limbs of different curvatures and sizes.

The orthopedic therapy apparatus 100 may include a deformable textile body 102 having an adhesion surface 104 and a non-adhesion surface (not shown) opposite to the adhesion surface 104. The adhesion surface 104 may include an adhesive, such as medical grade acrylic adhesive, which may be hypoallergenic. The deformable textile body 102 may be made of a deformable textile material of uniform thickness.

In some aspects, the deformable textile material may include cotton or 100% natural fibers. In other aspects, the deformable textile material may include nonwoven fabrics, woven fabrics, high twist fabrics containing high twist yarn, elastic fabric using elastic yarn, nylon, polyester, polyurethane, rayon, polypropylene, polyethylene, and/or the like.

In one or more aspects, the deformable textile material may have a higher elasticity along a deformable textile body longitudinal axis and a lower elasticity along a deformable textile body latitudinal axis. In other words, the deformable textile body 102 may be more stretchable along the deformable textile body longitudinal axis (e.g., along a deformable textile body length) than the deformable textile body latitudinal axis (e.g., along a deformable textile body width).

In some aspects, the orthopedic therapy apparatus 100, specifically the adhesion surface 104, may include a first adhesion pad surface 106, a second adhesion pad surface 108, and a third adhesion surface 110. In some aspects, the first adhesion pad surface 106, the second adhesion pad surface 108 and the third adhesion surface 110 may be disposed on the adhesion surface 104. In other aspects, the first adhesion pad surface 106, the second adhesion pad surface 108 and the third adhesion surface 110 may be a part of the adhesion surface 104.

As shown in FIG. 1, the first adhesion pad surface 106 may be disposed at a deformable textile body proximal end, the second adhesion pad surface 108 may be disposed at a deformable textile body distal end, and the third adhesion surface 110 may be disposed between the first adhesion pad surface 106 and the second adhesion pad surface 108. In other words, the first adhesion pad surface 106 and the second adhesion pad surface 108 may be present at deformable textile body sides, and the third adhesion surface 110 may be present at a deformable textile body middle.

In further aspects, the third adhesion surface 110 may include (or divided into) a first adhesion surface side portion 112a, a first deformable textile body middle portion 112b, a second deformable textile body middle portion 112c and a second adhesion surface side portion 112d. In some aspects, the portions 112a, 112b, 112c, and 112d are parallel to each other or disposed along a deformable textile body longitudinal axis. As shown, the first adhesion surface side portion 112a may be disposed proximate to an orthopedic therapy apparatus edge along the deformable textile body longitudinal axis, and the second adhesion surface side portion 112d may be disposed proximate to an orthopedic therapy apparatus opposite edge along the deformable textile body longitudinal axis. Further, the portions 112a, 112b, 112c, and 112d may be disposed between the first adhesion pad surface 106 and the second adhesion pad surface 108. In further aspects, the portions 112a, 112b, 112c, and 112d may have an equal width.

The orthopedic therapy apparatus 100 may further include a first pair of separating cuts 114a, 114b formed on the deformable textile body 102 and adjacent to the first adhesion pad surface 106. The first pair of separating cuts 114a, 114b may be formed proximate to the deformable textile body proximal end. In some aspects, the separating cut 114a may be formed on the first adhesion surface side portion 112a and the separating cut 114b may be formed on the second adhesion surface side portion 112d.

The orthopedic therapy apparatus 100 may further include a second pair of separating cuts 114c and 114d formed on the deformable textile body 102 and adjacent to the second adhesion pad surface 108. The second pair of separating cuts 114c and 114d may be formed proximate to the deformable textile body distal end. In some aspects, the separating cut 114c may be formed on the first adhesion surface side portion 112a, and the separating cut 114d may be formed on the second adhesion surface side portion 112d.

The separating cuts 114a, 114b, 114c, and 114d may be used to fold the first adhesion surface side portion 112a on the first deformable textile body middle portion 112b, and to fold the second adhesion surface side portion 112d on the second deformable textile body middle portion 112c. In some aspects, the separating cuts 114a, 114b, 114c, and 114d may be slanted at a predetermined angle from the deformable textile body longitudinal axis. For example, the separating cuts 114a, 114b, 114c, and 114d may be slanted at an angle of 45 degrees (as shown in FIG. 1), or at 30 degrees, 60 degrees, or 90 degrees.

A separating cut length 116 of each separating cuts 114a, 114b, 114c, and 114d may vary based on the predetermined angle. In further aspects, the separating cut length 116 may be based on orthopedic therapy apparatus dimensions. For example, the separating cut length 116 may be based on the deformable textile body width. In some aspects, the separating cut length 116 of each separating cuts 114a, 114b, 114c, and 114d may be equal.

In one or more aspects, the first adhesion surface side portion 112a and the second adhesion surface side portion 112d may be folded around the deformable textile body longitudinal axis. Specifically, the first adhesion surface side portion 112a may be folded to contact and adhere to the first deformable textile body middle portion 112b, and the second adhesion surface side portion 112d may be folded to contact and adhere to the second deformable textile body middle portion 112c. As discussed above, the first adhesion surface side portion 112a and the second adhesion surface side portion 112d may be folded by using the first pair of separating cuts 114a, 114b and the second pair of separating cuts 114c, 114d.

As shown in FIG. 1, the first adhesion surface side portion 112a and the second adhesion surface side portion 112d may fold such that the edges of the first adhesion surface side portion 112a and the second adhesion surface side portion 112d may contact each other, and adhere to a deformable textile body middle portion (such as the first deformable textile body middle portion 112b and the second deformable textile body middle portion 112c).

In one or more aspects, an entire area of the first adhesion surface side portion 112a, the first deformable textile body middle portion 112b, the second deformable textile body middle portion 112c and the second adhesion surface side portion 112d may not include adhesive. For example, in some aspects, only the first adhesion surface side portion 112a and the second adhesion surface side portion 112d may include adhesive. In other aspects, only the first deformable textile body middle portion 112b and the second deformable textile body middle portion 112c may include adhesive. In yet another aspect, as described above, the entire area of the first adhesion surface side portion 112a, the first deformable textile body middle portion 112b, the second deformable textile body middle portion 112c and the second adhesion surface side portion 112d may include adhesive.

In some aspects, a folded first adhesion surface side portion and a folded second adhesion surface side portion may form an orthopedic therapy apparatus tension member. The tension member may be disposed on the adhesion surface 104, and may be formed between the first adhesion pad surface 106 and the second adhesion pad surface 108. The tension member is described in conjunction with FIGS. 2A and 2B.

In some aspects, a tension member length 122 (along the deformable textile body longitudinal axis) may be greater than a first adhesion pad surface length 118 and/or a second adhesion pad surface length 120. In other aspects, the tension member length 122 may be smaller or same as the first adhesion pad surface length 118 and/or the second adhesion pad surface length 120.

The first adhesion pad surface length 118, the second adhesion pad surface length 120, and the tension member length 122 may vary based on a user/patient requirement or limb size. For example, the tension member length 122 may be 2.1 inches, 4 inches, 6 inches, or 10 inches. The corresponding example first adhesion pad surface length 118 and the second adhesion pad surface length 120 may be 1.4 inches, 1.18 inches, 1.57 inches, or 2.36 inches. In some aspects, the first adhesion pad surface length 118 and the second adhesion pad surface length 120 may be same or similar.

A person ordinarily skilled in the art may appreciate that the example lengths described above are not intended to be limiting, and the first adhesion pad surface length 118, the second adhesion pad surface length 120, and the tension member length 122 may have different dimensions, without departing from the present disclosure scope.

The orthopedic therapy apparatus 100 may further include a first protective cover (not shown) removably disposed over the first adhesion pad surface 106, and a second protective cover 124 removably disposed over the second adhesion pad surface 108. In some aspects, the first protective cover and the second protective cover 124 may include a backing film/material that protects the first adhesion pad surface 106 and the second adhesion pad surface 108 from ambient environment.

The first proactive cover and the second protective cover 124 exposes the first adhesion pad surface 106 and the second adhesion pad surface 108 when the first proactive cover and the second protective cover 124 are removed. A therapist may apply the orthopedic therapy apparatus 100 to a user skin (e.g., to the patient limb) by removing the first proactive cover and the second protective cover 124, and then attaching the first adhesion pad surface 106 and the second adhesion pad surface 108 to the user skin.

Specifically, in operation, the therapist may first fold the first adhesion surface side portion 112a and the second adhesion surface side portion 112d to form the tension member (as described above), and may then remove the first proactive cover and the second protective cover 124. Thereafter, the therapist may apply the orthopedic therapy apparatus 100 to the user skin.

In some aspects, the orthopedic therapy apparatus 100 may further include a third protective cover (not shown) disposed over the first adhesion surface side portion 112a, the first deformable textile body middle portion 112b, the second deformable textile body middle portion 112c and the second adhesion surface side portion 112d. In additional aspects, the first proactive cover, the second protective cover 124 and the third protective cover may be part of a single protective cover protecting the adhesion surface 104. In this case, the therapist may first remove the single protective cover, fold the first adhesion surface side portion 112a and the second adhesion surface side portion 112d, and may then apply the orthopedic therapy apparatus 100 to the user skin by using the first adhesion pad surface 106 and the second adhesion pad surface 108.

Figure 2A:
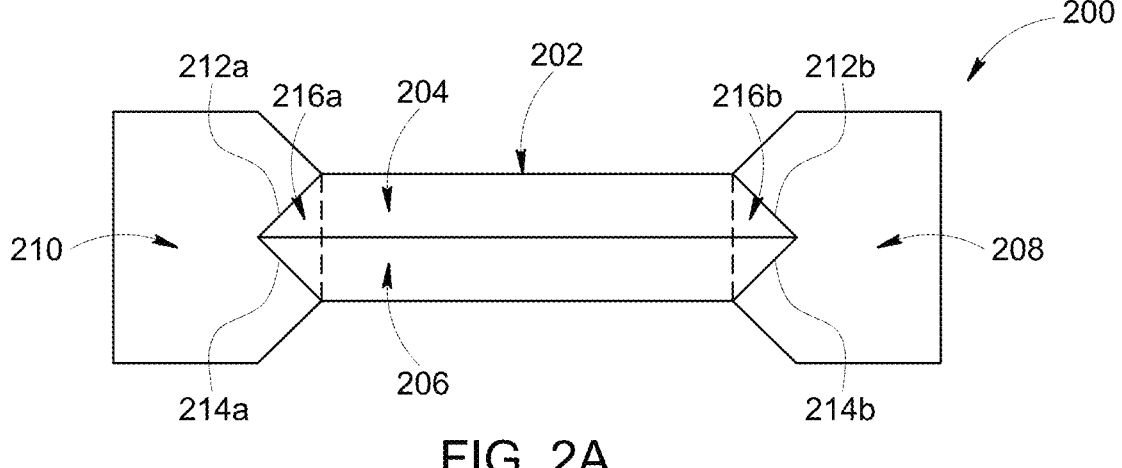
FIG. 2A depicts a folded orthopedic therapy apparatus of FIG. 1 in accordance with the present disclosure.

FIG. 2A depicts a folded orthopedic therapy apparatus 200 of FIG. 1 in accordance with the present disclosure. The orthopedic therapy apparatus 200 may be same as the orthopedic therapy apparatus 100. In other words, FIG. 2A depicts a folded view of the orthopedic therapy apparatus 100.

The orthopedic therapy apparatus 200 may include a tension member 202 that may be formed from a folded first side portion 204 and a folded second side portion 206, as described above. The folded first side portion 204 and the folded second side portion 206 may be formed by folding the first adhesion surface side portion 112a and the second adhesion surface side portion 112d.

A person ordinarily skilled in the art may appreciate that since the tension member 202 is formed from the folded first side portion 204 and the folded second side portion 206, the tension member 202 and the deformable textile body 102 are formed from a single length of deformable textile member. In other words, since the folded first side portion 204 and the folded second side portion 206 is formed from the deformable textile body 102, the tension member 202 may also be formed of same length or strip of the deformable textile member as the deformable textile body 102.

The orthopedic therapy apparatus 200 may further include a first adhesion pad surface 208 formed at an orthopedic therapy apparatus proximal end, and a second adhesion pad surface 210 formed at an orthopedic therapy apparatus distal end. The first adhesion pad surface 208 and the second adhesion pad surface 210 may be same as the first adhesion pad surface 106 and the second adhesion pad surface 108.

As described above, the therapist may apply the orthopedic therapy apparatus 200 to the patient limb by using the first adhesion pad surface 208 and the second adhesion pad surface 210. Since the tension member surface that touches the patient limb does not include adhesive surface (since the folded first side portion 204 and the folded second side portion 206 includes the deformable textile body non-adhesive surface), the orthopedic therapy apparatus 200 may be more convenient to use for a patient, as compared to a conventional orthopedic therapy tape. In other words, of the three surfaces that touch the patient limb, i.e., the tension member 202, the first adhesion pad surface 208 and the second adhesion pad surface 210, only the first adhesion pad surface 208 and the second adhesion pad surface 210 may have adhesive surfaces, and the tension member 202 may include cloth. Therefore, the orthopedic therapy apparatus 200 may be more convenient to use for a patient for longer duration, as the tension member cloth fabric may be comfortable than conventional orthopedic therapy tape adhesives.

In some aspects, a first adhesion pad surface width and a second adhesion pad surface width may be double a tension member width. Further, the tension member 202 may include folded first side portion distal and proximal edges 212a, 212b, and folded second side portion distal and proximal edges 214a, 214b. Since the folded first and second side portions 204, 206 are formed by folding the first and second adhesion surface side portions 112a, 112d by using the first and second pair of separating cuts 114a, 114b, 114c, 114d (which are slanted at the predetermined angle), the folded first and second side portion proximal and distal edges 212a, 212b, 214a, 214b too are slanted at the predetermined angle. Specifically, the folded first and second side portion distal and proximal edges 212a, 212b, 214a, 214b may be slanted at the predetermined angle from the deformable textile body longitudinal axis.

A person ordinarily skilled in the art may appreciate that since the first and second pair of separating cuts 114a, 114b, 114c, 114d are slanted at the predetermined angle, the folded first and second side portion proximal and distal edges 212a, 212b, 214a, 214b form a triangular shape, as shown as shapes 216a, 216b in FIG. 2. Based on the predetermined angle, the triangular shape may have different top vertex angles. For example, if the predetermined angle is 45 degrees or 90 degrees, the triangular shape top vertex angle may be 90 degrees or 180 degrees, respectively. In the latter case, the folded first and second side portion proximal and distal edges 212a, 212b, 214a, 214b may form a straight line (and not a triangular shape).

In some aspects, the therapist may cut the folded first and second side portion proximal and distal edges 212a, 212b, 214a, 214b (if the predetermined angle is not 90 degrees) before applying the orthopedic therapy apparatus 200 to the patient limb. In other aspects, the therapist may apply the orthopedic therapy apparatus 200 to the patient limb without cutting the folded first and second side portion proximal and distal edges 212a, 212b, 214a, 214b.

Figure 2B:
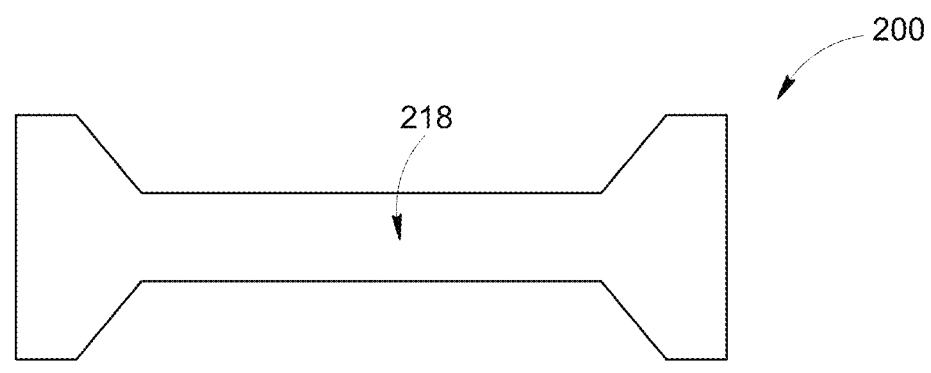
FIG. 2B depicts a front view of the folded orthopedic therapy apparatus of FIG. 2A in accordance with the present disclosure.

FIG. 2B depicts a front view of the folded orthopedic therapy apparatus 200 of FIG. 2A in accordance with the present disclosure. Specifically, FIG. 2B depicts a view opposite to the orthopedic therapy apparatus view depicted in FIG. 2A. In particular, FIG. 2B depicts an orthopedic therapy apparatus outer view (which may be visible to the patient and/or the therapist) when the therapist folds the first adhesion surface side portion 112a and the second adhesion surface side portion 112d, and applies the orthopedic therapy apparatus 200 to the patient limb.

The orthopedic therapy apparatus outer/front surface may include a non-adhesive surface 218. In some aspects, the non-adhesive surface 218 may include cotton or 100% natural fibers. In some aspects, the non-adhesive surface 218 may be made of same material as the tension member 202.

Figure 3A:
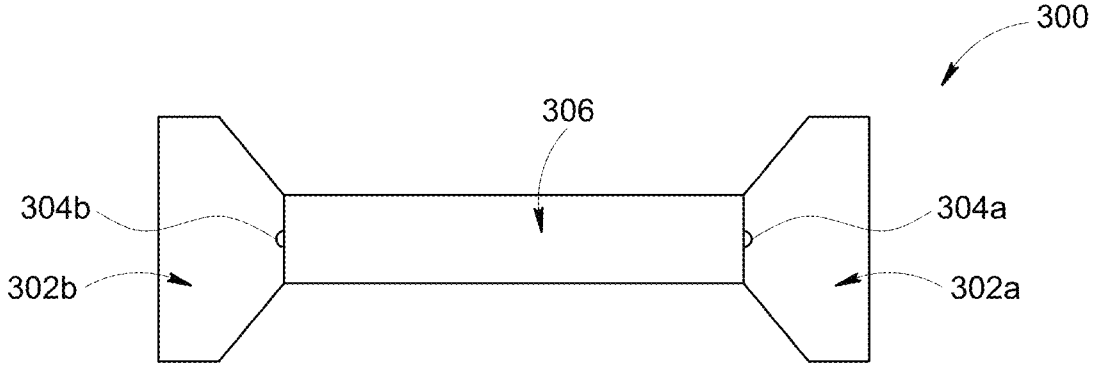
FIG. 3A depicts a back view of an orthopedic therapy apparatus with protective covers, in accordance with the present disclosure.

FIG. 3A depicts a back view of an orthopedic therapy apparatus 300 with protective covers 302a, 302b, in accordance with the present disclosure. The orthopedic therapy apparatus 300 may be same as the orthopedic therapy apparatus 100 or 200, and the protective covers 302a, 302b may be same as the first protective cover and the second protective cover 124. As described above, the protective covers 302a, 302b may be disposed over the first adhesion pad surface 106 and the second adhesion pad surface 108. The protective covers 302a, 302b may protect the first adhesion pad surface 106 and the second adhesion pad surface 108 from ambient environment.

In some aspects, the protective covers 302a, 302b may include opening slots 304a, 304b disposed on the protective covers 302a, 302b. In one or more aspects, the opening slots 304a, 304b may be disposed adjacent to side edges of a tension member 306, as shown in FIG. 3A. In other aspects, the opening slots 304a, 304b may be disposed at one or more protective cover corners. In yet another aspect, the opening slots 304a, 304b may be elongated cuts that may be provided along protective cover longitudinal or latitudinal axis.

The opening slots 304a, 304b may enable/assist the therapist to conveniently remove the protective covers 302a, 302b, before applying the orthopedic therapy apparatus 300 to the patient limb. For example, the therapist may remove the protective covers 302a, 302b by inserting a finger into the opening slots 304a, 304b, and lifting the opening slots 304a, 304b. Alternatively, the therapist may be use a medical tuning fork to lift the opening slots 304a, 304b.

Figure 3B:
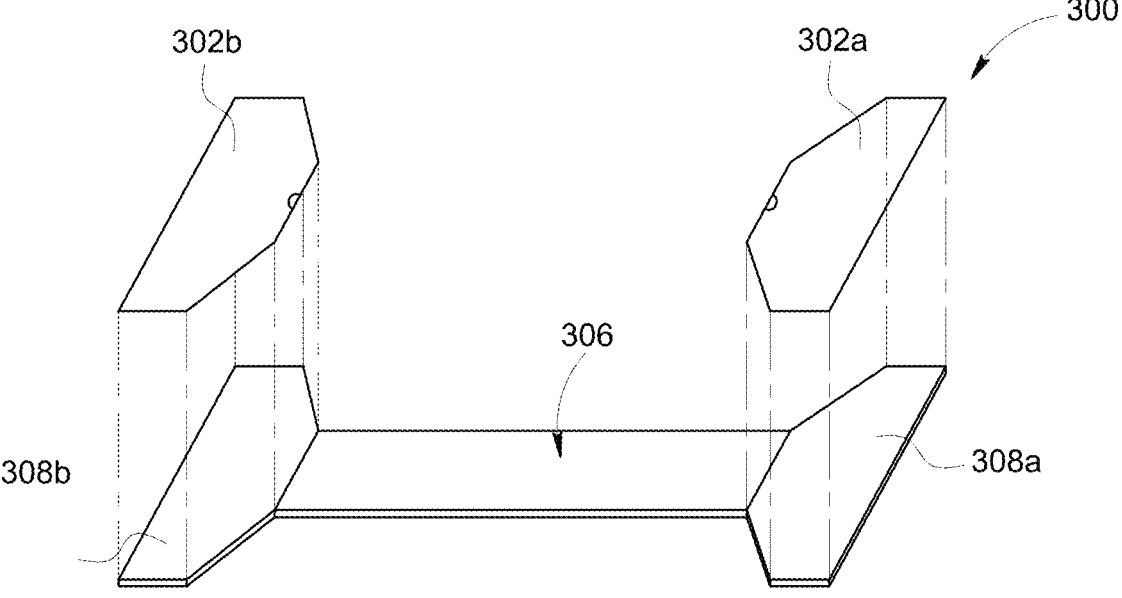
FIG. 3B depicts an exploded view of the orthopedic therapy apparatus of FIG. 3A with the protective covers removed, in accordance with the present disclosure.

FIG. 3B depicts an exploded view of the orthopedic therapy apparatus 300 of FIG. 3A with the protective covers 302a, 302b removed, in accordance with the present disclosure. As described above, the therapist may remove the protective covers 302a, 302b to expose a first adhesion pad surface 308a and a second adhesion pad surface 308b, and apply the orthopedic therapy apparatus 300 to the patient limb by using the first adhesion pad surface 308a and the second adhesion pad surface 308b. The first adhesion pad surface 308a and the second adhesion pad surface 308b may be same as the first adhesion pad surface 106 and the second adhesion pad surface 108.

Figure 4A:
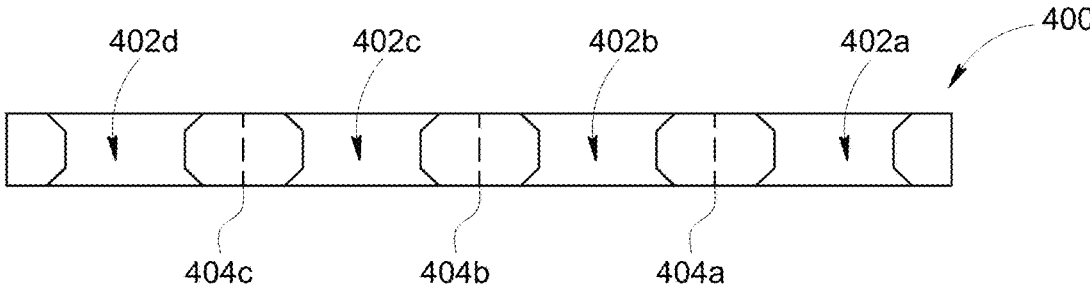
FIG. 4A depicts a customizable orthopedic therapy apparatus in accordance with the present disclosure.

FIG. 4A depicts a customizable orthopedic therapy apparatus 400 in accordance with the present disclosure. The customizable orthopedic therapy apparatus 400 may include a plurality of elongated orthopedic therapy tapes 402a, 402b, 402c and 402d. In some aspects, each elongated orthopedic therapy tape 402a, 402b, 402c or 402d may be same as the orthopedic therapy apparatus 100, 200 or 300. In some aspects, the customizable orthopedic therapy apparatus 400 may include a strip of the plurality of elongated orthopedic therapy tapes 402a, 402b, 402c, 402d, as shown in FIG. 4A. In other aspects, the customizable orthopedic therapy apparatus 400 may include a stack or a roll of the plurality of elongated orthopedic therapy tapes 402a, 402b, 402c, and 402d.

As described above, each elongated orthopedic therapy tape may include a plurality of components, such as a deformable textile body having an adhesion surface and a non-adhesion surface, a first adhesion pad surface, a second adhesion pad surface, separating cuts, a first adhesion surface side portion, a second adhesion surface side portion, a tension member, and the like. Since elongated orthopedic therapy tape structure is same as the orthopedic therapy apparatus structure described in conjunction with FIG. 1, the elongated therapy tape structure is not described again for the sake of simplicity.

In some aspects, the customizable orthopedic therapy apparatus 400 may include a plurality of cut guides 404a, 404b, 404c, when the customizable orthopedic therapy apparatus 400 includes a strip of the plurality of elongated orthopedic therapy tapes 402a, 402b, 402c, 402d, as shown in FIG. 4A. In some aspects, the plurality of cut guides 404a, 404b, 404c may be disposed over a protective film/cover (not shown) that may be disposed over a customizable orthopedic therapy apparatus area (e.g., the entire area). In other aspects, the plurality of cut guides 404a, 404b, 404c may be disposed over an adhesive surface of the customizable orthopedic therapy apparatus deformable textile body.

As shown in FIG. 4A, the plurality of cut guides 404a, 404b, 404c may be disposed perpendicular to a deformable textile body longitudinal axis, and each cut guide may be disposed at a predetermined distance from adjacent cut guides.

The therapist may customize a customizable orthopedic therapy apparatus length by cutting the customizable orthopedic therapy apparatus 400 along a cut guide or a pair of cut guides. For example, if the therapist applies the customizable orthopedic therapy apparatus 400 over a patient leg or arm, the therapist may cut the customizable orthopedic therapy apparatus 400 along the cut guides 404a and 404c. On the other hand, if the therapist applies the customizable orthopedic therapy apparatus 400 over a patient finger, the therapist may cut the customizable orthopedic therapy apparatus 400 along the cut guides 404a and 404b (since shorter length may be required to cover the patient finger).

In one or more aspects, if the plurality of cut guides 404a, 404b, 404c is disposed over the customizable orthopedic therapy apparatus protective film/cover, the therapist may first cut the customizable orthopedic therapy apparatus 400 by using a cut guide or a pair of cut guides, and may then remove the protective film/cover.

Figure 4B:
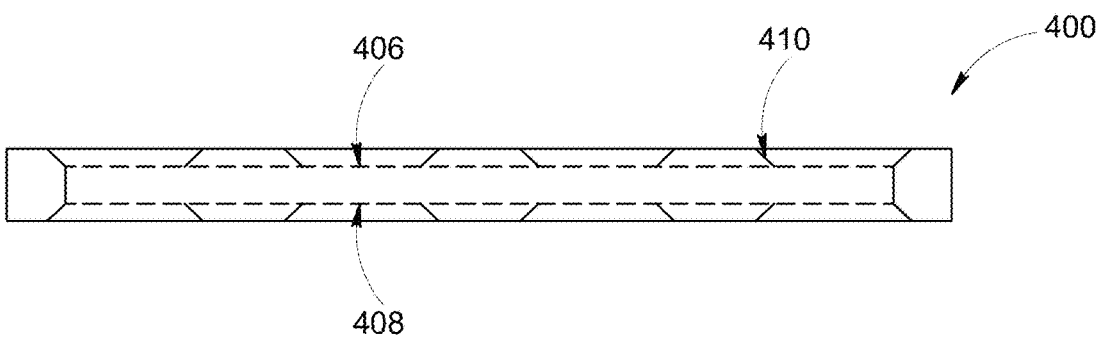
FIG. 4B depicts the customizable orthopedic therapy apparatus of FIG. 4A with protective covers removed, in accordance with the present disclosure.

FIG. 4B depicts the customizable orthopedic therapy apparatus 400 of FIG. 4A with the protective cover removed, in accordance with the present disclosure. In some aspects, the protective cover may be removed from the orthopedic therapy apparatus area (such as the entire area).

In some aspects, the therapist may fold a first adhesion surface side portion 406 and a second adhesion surface side portion 408 around the customizable orthopedic therapy apparatus longitudinal axis, after removing the protective cover/film. As described above, the the therapist may fold the first adhesion surface side portion 406 and the second adhesion surface side portion 408 by using a plurality of separating cuts 410 (shown as a separating cut 410 in FIG. 4B).

Figure 4C:
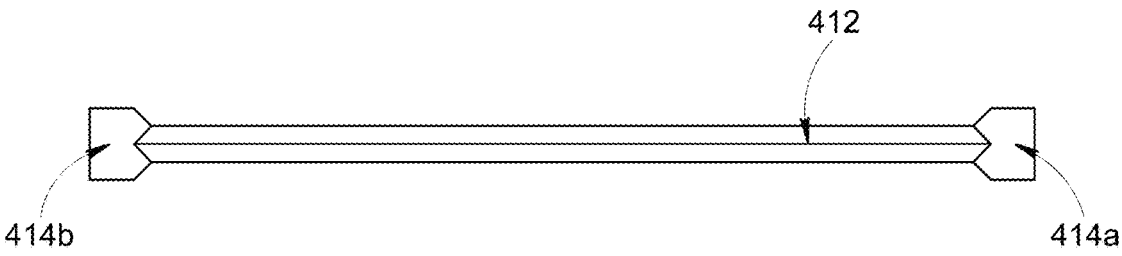
FIG. 4C depicts a folded customizable orthopedic therapy apparatus of FIG. 4B in accordance with the present disclosure.

FIG. 4C depicts a folded customizable orthopedic therapy apparatus 400 of FIG. 4B in accordance with the present disclosure. As described above in conjunction with FIG. 1 and FIG. 2, a folded first adhesion surface side portion and a folded second adhesion surface side portion may form a tension member 412. The therapist may apply the customizable orthopedic therapy apparatus 400 to the patient limb by using a first and a second adhesive pad surfaces 414a and 414b.

In some aspects, the customizable orthopedic therapy apparatus 400 may include additional or separate protective covers over the first and second adhesive pad surfaces 414a, 414b. In this case, the therapist may first remove the additional/separate protective covers, before applying the customizable orthopedic therapy apparatus 400 to the patient limb. In other aspects, the customizable orthopedic therapy apparatus 400 may include a single protective cover/film for the customizable orthopedic therapy apparatus 400 (and no separate protective covers for the first and second adhesive pad surfaces 414a and 414b).

Figures 5A, 5B, 5C:
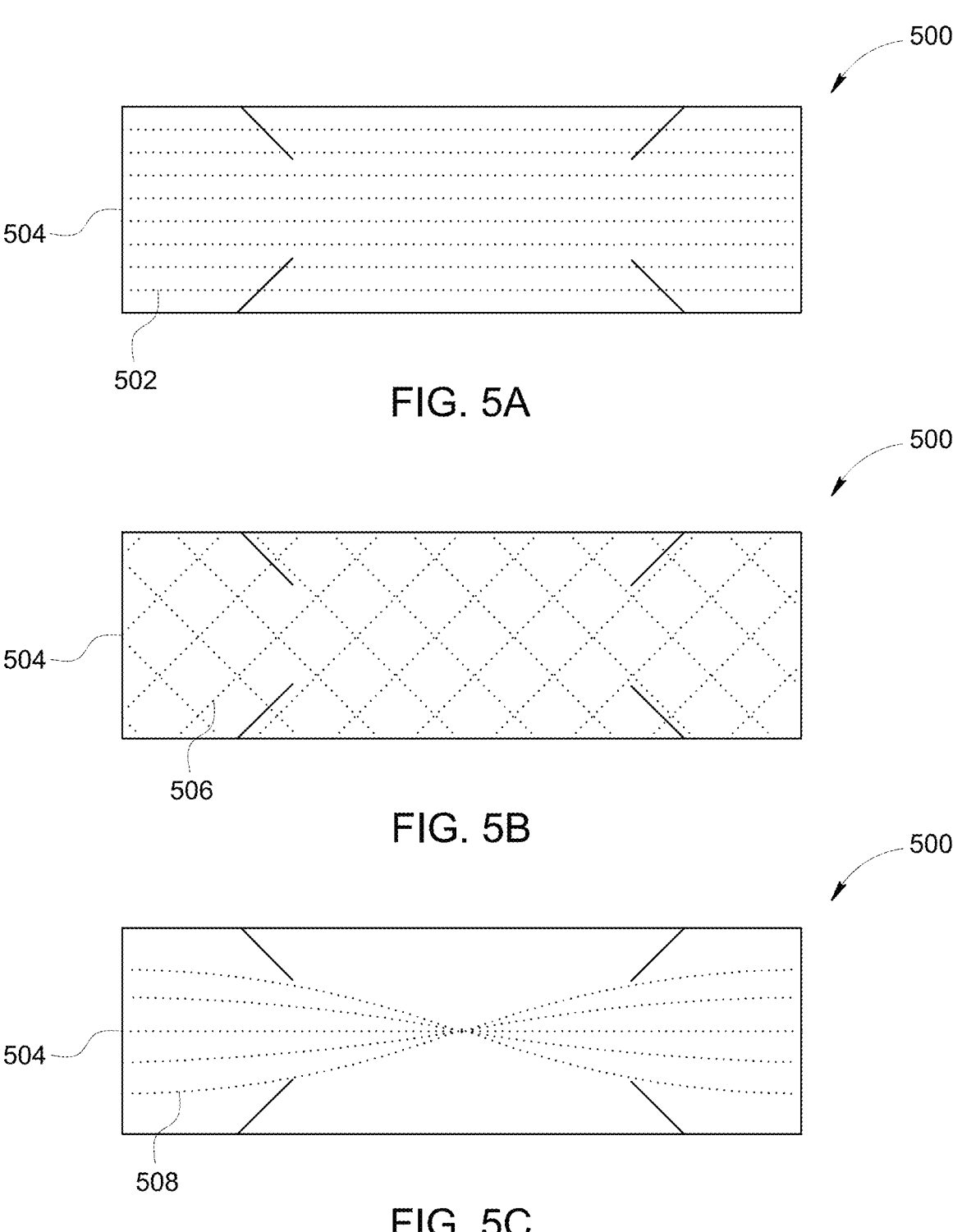
FIGS. 5A, 5B and 5C depict an example orthopedic therapy apparatus having a plurality of elongated threads, in accordance with the present disclosure.

FIGS. 5A, 5B and 5C depict an example orthopedic therapy apparatus 500 having a plurality of elongated threads, in accordance with the present disclosure. Specifically, FIG. 5A depicts a plurality of elongated threads 502 formed on a deformable textile body 504. In some aspects, the orthopedic therapy apparatus 500 may be same as the orthopedic therapy apparatus 100 and the deformable textile body 504 may be same as the deformable textile body 102.

The plurality of elongated threads 502 may be linear threads that may be formed along a deformable textile body longitudinal axis. In some aspects, the plurality of elongated threads 502 may be formed parallel to deformable textile body longitudinal edges, as shown in FIG. 5A. The plurality of elongated threads 502 may be made of same material as the deformable textile material (e.g., cloth), or may be made of a different material (e.g., nylon, polyester, etc.). The plurality of elongated threads 502 may provide threaded reinforcement to the patient, when the patient moves with the orthopedic therapy apparatus 500 applied to the patient limb. For example, the plurality of elongated threads 502 may help maintain tension (e.g., by reducing longitudinal elongation) in the orthopedic therapy apparatus 500 when the patient performs physical activities (e.g., exercise) that might cause limb movement.

Depending on orthopedic therapy apparatus dimensions, a number of elongated threads in the deformable textile body 504 may increase or decrease. For example, although eight elongated threads are shown in FIG. 5A, a person ordinarily skilled in the art may appreciate that more (or less) elongated threads may be formed on the deformable textile body 504.

In some aspects, the elongated threads may be formed in different configurations, e.g., cross-hatched configuration, lateral configuration, straight X-shaped configuration or curved X-shaped configuration. FIG. 5B depicts a plurality of elongated threads 506 formed in a cross-hatched configuration. Further, FIG. 5C depicts a plurality of elongated threads 508 formed in a curved X-shaped configuration.

The configurations shown in FIGS. 5B and 5C may assist in reducing elongation along an angular direction of the deformable textile body 504. Further, a separate elongated thread configuration, which may be a combination of one or more configurations shown in FIGS. 5A, 5B and 5C, may be formed on the deformable textile body 504.

Figure 6:
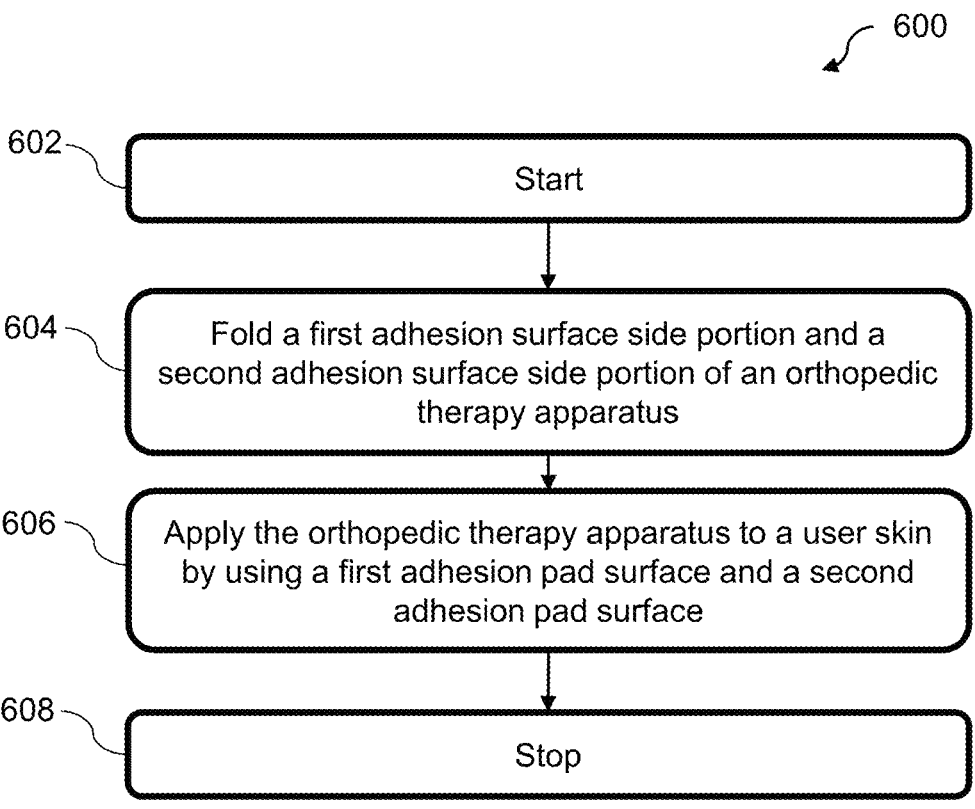
FIG. 6 depicts a flow diagram of a method for applying an orthopedic therapy apparatus to a user skin in accordance with the present disclosure.

FIG. 6 depicts a flow diagram of a method 600 for applying an orthopedic therapy apparatus to a user skin in accordance with the present disclosure. The orthopedic therapy apparatus may be, for example, the orthopedic therapy apparatus 100 or 500 described in conjunction with FIG. 1 and FIGS. 5A, 5B and 5C, or the customizable orthopedic therapy apparatus 400 described in conjunction with FIGS. 4A and 4B. FIG. 6 may be described with continued reference to prior figures. The following process is exemplary and not confined to the steps described hereafter. Moreover, alternative embodiments may include more or less steps that are shown or described herein and may include these steps in a different order than the order described in the following example embodiments.

At step 602, the method 600 may commence. At step 604, the method 600 may include folding the first adhesion surface side portion 112*a* and the second adhesion surface side portion 112*d* around the deformable textile body longitudinal axis by using the first pair of separating cuts 114*a*, 114*b* and the second pair of separating cuts 114*c*, 114*d*. As described above, the therapist may fold the first adhesion surface side portion 112*a* and the second adhesion surface side portion 112*d* to contact and adhere to the deformable textile body middle portion to form the tension member 202.

At step 606, the method 600 may include applying the orthopedic therapy apparatus 100 to a user skin (e.g., the patient limb) by using the first adhesion pad surface 106 and the second adhesion pad surface 108.

At step 608, the method 600 may end.

The method 600 may include additional steps that are not shown in FIG. 6. For example, the method 600 may include a step of cutting the customized orthopedic therapy apparatus 400 by using a cut guide or a pair of cut guides, before folding the first adhesion surface side portion 112*a* and the second adhesion surface side portion 112*d*. Further, the method 600 may include a step of removing the protective film, and/or the first protective cover and the second protective cover 124, before applying the orthopedic therapy apparatus 100 to the user skin.

In the above disclosure, reference has been made to the accompanying drawings, which form a part hereof, which illustrate specific implementations in which the present disclosure may be practiced. It is understood that other implementations may be utilized, and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a feature, structure, or characteristic is described in connection with an embodiment, one skilled in the art will recognize such feature, structure, or characteristic in connection with other embodiments whether or not explicitly described.

It should also be understood that the word "example" as used herein is intended to be non-exclusionary and non-limiting in nature. More particularly, the word "example" as used herein indicates one among several examples, and it should be understood that no undue emphasis or preference is being directed to the particular example being described.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating various embodiments and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their ordinary meanings as understood by those knowledgeable in the technologies described herein unless an explicit indication to the contrary is made herein. In particular, use of the singular articles such as "a," "the," "said," etc., should be read to recite one or more of the indicated elements unless a claim recites an explicit limitation to the contrary. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. An orthopedic therapy apparatus having a plurality of elongated therapy tapes, wherein each elongated therapy tape comprises:

a deformable textile body comprising an adhesion surface and a non-adhesion surface opposite to the adhesion surface;

a first adhesion pad surface disposed on the adhesion surface at a deformable textile body proximal end;

a second adhesion pad surface disposed on the adhesion surface at a deformable textile body distal end;

a first adhesion surface side portion disposed proximate to an orthopedic therapy apparatus edge along a deformable textile body longitudinal axis, wherein the first adhesion surface side portion is disposed between the first adhesion pad surface and the second adhesion pad surface;

a second adhesion surface side portion disposed proximate to an orthopedic therapy apparatus opposite edge along the deformable textile body longitudinal axis, wherein the second adhesion surface side portion is disposed between the first adhesion pad surface and the second adhesion pad surface; and a first pair of separating cuts proximate to the deformable textile body proximal end, and a second pair of separating cuts proximate to the deformable textile body distal end, wherein the first adhesion surface side portion and the second adhesion surface side portion are configured to be folded around the deformable textile body longitudinal axis by using the first pair of separating cuts and the second pair of separating cuts, wherein the first adhesion surface side portion and the second adhesion surface side portion fold to contact and adhere to a deformable textile body middle portion to form a tension member, and wherein the deformable textile body and the tension member are comprised of a single length of a deformable textile material.

2. The orthopedic therapy apparatus of claim 1, wherein the first adhesion surface side portion folds to contact and adhere to a first deformable textile body middle portion.

3. The orthopedic therapy apparatus of claim 1, wherein the second adhesion surface side portion folds to contact and adhere to a second deformable textile body middle portion.

4. The orthopedic therapy apparatus of claim 1, wherein the plurality of elongated therapy tapes is separated by a plurality of cut guides, and wherein each cut guide is disposed perpendicular to the deformable textile body longitudinal axis.

5. The orthopedic therapy apparatus of claim 4, wherein each cut guide is disposed at a predetermined distance from adjacent cut guides.

6. The orthopedic therapy apparatus of claim 1, wherein the first pair of separating cuts and the second pair of separating cuts are slanted at a predetermined angle from the deformable textile body longitudinal axis.

7. The orthopedic therapy apparatus of claim 6, wherein the predetermined angle is 45 degrees.

8. The orthopedic therapy apparatus of claim 1 further comprising a protective film disposed on the adhesive surface.

9. The orthopedic therapy apparatus of claim 1, wherein the tension member is disposed between the first adhesion pad surface and the second adhesion pad surface.

10. The orthopedic therapy apparatus of claim 1 further comprising a plurality of elongated threads formed on the deformable textile body.

11. The orthopedic therapy apparatus of claim 10, wherein the plurality of elongated threads are linear threads formed along the deformable textile body longitudinal axis.

12. The orthopedic therapy apparatus of claim 10, wherein the plurality of elongated threads is formed in a cross-hatched configuration.

13. The orthopedic therapy apparatus of claim 10, wherein the plurality of elongated threads is formed in a curved X-shaped configuration.

14. An orthopedic therapy apparatus having a plurality of elongated therapy tapes, wherein each elongated therapy tape comprises:

a deformable textile body comprising an adhesion surface and a non-adhesion surface opposite to the adhesion surface;

a plurality of elongated threads formed on the deformable textile body;

a first adhesion pad surface disposed on the adhesion surface at a deformable textile body proximal end;

a second adhesion pad surface disposed on the adhesion surface at a deformable textile body distal end;

a first adhesion surface side portion disposed proximate to an orthopedic therapy apparatus edge along a deformable textile body longitudinal axis, wherein the first adhesion surface side portion is disposed between the first adhesion pad surface and the second adhesion pad surface;

a second adhesion surface side portion disposed proximate to an orthopedic therapy apparatus opposite edge along the deformable textile body longitudinal axis, wherein the second adhesion surface side portion is disposed between the first adhesion pad surface and the second adhesion pad surface; and a first pair of separating cuts proximate to the deformable textile body proximal end, and a second pair of separating cuts proximate to the deformable textile body distal end, wherein the first adhesion surface side portion and the second adhesion surface side portion are configured to be folded around the deformable textile body longitudinal axis by using the first pair of separating cuts and the second pair of separating cuts, wherein the first adhesion surface side portion and the second adhesion surface side portion fold to contact and adhere to a deformable textile body middle portion to form a tension member, and wherein the deformable textile body and the tension member are comprised of a single length of a deformable textile material.

15. The orthopedic therapy apparatus of claim 14, wherein the first adhesion surface side portion folds to contact and adhere to a first deformable textile body middle portion.

16. The orthopedic therapy apparatus of claim 14, wherein the second adhesion surface side portion folds to contact and adhere to a second deformable textile body middle portion.

17. The orthopedic therapy apparatus of claim 14, wherein the plurality of elongated therapy tapes is separated by a plurality of cut guides, and wherein each cut guide is disposed perpendicular to the deformable textile body longitudinal axis.

18. The orthopedic therapy apparatus of claim 17, wherein each cut guide is disposed at a predetermined distance from adjacent cut guides.

19. The orthopedic therapy apparatus of claim 14, wherein the first pair of separating cuts and the second pair of separating cuts are slanted at a predetermined angle from the deformable textile body longitudinal axis.

20. An orthopedic therapy apparatus having a plurality of elongated therapy tapes, wherein each elongated therapy tape comprises:

a deformable textile body comprising an adhesion surface and a non-adhesion surface opposite to the adhesion surface;

a first adhesion pad surface disposed on the adhesion surface at a deformable textile body proximal end;

a second adhesion pad surface disposed on the adhesion surface at a deformable textile body distal end;

a first adhesion surface side portion disposed proximate to an orthopedic therapy apparatus edge along a deformable textile body longitudinal axis, wherein the first adhesion surface side portion is disposed between the first adhesion pad surface and the second adhesion pad surface;

a second adhesion surface side portion disposed proximate to an orthopedic therapy apparatus opposite edge along the deformable textile body longitudinal axis, wherein the second adhesion surface side portion is disposed between the first adhesion pad surface and the second adhesion pad surface; and a first pair of separating cuts proximate to the deformable textile body proximal end, and a second pair of separating cuts proximate to the deformable textile body distal end, wherein the first adhesion surface side portion and the second adhesion surface side portion are configured to be folded around the deformable textile body longitudinal axis by using the first pair of separating cuts and the second pair of separating cuts,

wherein the first adhesion surface side portion and the
second adhesion surface side portion fold to contact
and adhere to a deformable textile body middle portion
to form a tension member, wherein the deformable textile body and the tension 5
member are comprised of a single length of a deform-
able textile material, wherein the plurality of elongated therapy tapes is sepa-
rated by a plurality of cut guides, and wherein each cut
guide is disposed perpendicular to the deformable 10
textile body longitudinal axis.

* * * * *

16